United States Patent [19]

Stetter et al.

[11] Patent Number: 5,047,073
[45] Date of Patent: Sep. 10, 1991

[54] SORPTION SEPARATION APPARATUS AND METHODS

[75] Inventors: Joseph R. Stetter; William R. Penrose, both of Naperville, Ill.

[73] Assignee: Transducer Research, Inc., Naperville, Ill.

[21] Appl. No.: 485,478

[22] Filed: Feb. 27, 1990

[51] Int. Cl.$^5$ .................................. B01D 15/03
[52] U.S. Cl. ............................. 55/18; 55/67; 55/197; 55/386
[58] Field of Search ............... 55/67, 197, 386, 18

[56] References Cited

U.S. PATENT DOCUMENTS

| | | | |
|---|---|---|---|
| 3,030,798 | 4/1962 | Lichtenfels | 55/197 X |
| 3,152,470 | 10/1964 | Reinecke et al. | 55/67 X |
| 3,494,105 | 2/1970 | Gil-Av et al. | 55/67 |
| 3,513,636 | 5/1970 | Halasz et al. | 55/197 |
| 3,513,637 | 5/1970 | Halasz et al. | 55/197 |
| 3,581,465 | 6/1971 | Haruki et al. | 55/67 |
| 3,790,348 | 2/1974 | Bassart et al. | 55/67 X |
| 3,926,589 | 12/1975 | Klementi et al. | 55/197 X |
| 4,001,111 | 1/1977 | Geissler et al. | 55/67 X |
| 4,154,583 | 5/1979 | Favre et al. | 55/197 X |
| 4,180,389 | 12/1979 | Paul | 55/197 X |
| 4,271,697 | 6/1981 | Mowery, Jr. | 55/67 X |
| 4,553,985 | 11/1985 | Dahlgren et al. | 55/67 |
| 4,704,141 | 11/1987 | Krebber | 55/197 |
| 4,873,058 | 10/1989 | Arnold et al. | 55/197 X |

FOREIGN PATENT DOCUMENTS 1272638   5/1972   United Kingdom ............... 55/197

Primary Examiner—Robert Spitzer
Attorney, Agent, or Firm—Solomon Zaromb

[57] ABSTRACT

Selective detection of an analyte in a gaseous mixture is achieved by a chemical, especially amperometric, sensor, that is responsive to the analyte, and a pump-and-valve system, controlled by programmed electronic circuitry, which causes: a) ambient air to pass first through a chemical filter, that removes those air constituents to which the sensor may be responsive, and next through a sorbent-containing tube and the sensor; b) a portion of the gaseous mixture to be first drawn into a sample port and next flushed from the port into the sorbent tube; c) analyte-containing eluent from the sorbent tube to reach the sensor; and d) another mixture component to which the sensor may be responsive to be prevented from reaching the sensor. The sorbent-containing tube has a different retentivity for the analyte than for the other mixture component. The air flow rates and paths can be programmed and the volume of the mixture portion may be auto-ranged to maximize the accuracy of the sensor signals. Speedy analyses of CO in the presence of $H_2$, of $H_2S$ in the presence of organosulfur interferences or of other volatiles, such as methanol, methylene chloride or formaldehyde in the presence of interfering compounds of heavier molecular weight are thereby achieved with a portable instrument having improved reliability and relatively low cost.

27 Claims, 3 Drawing Sheets

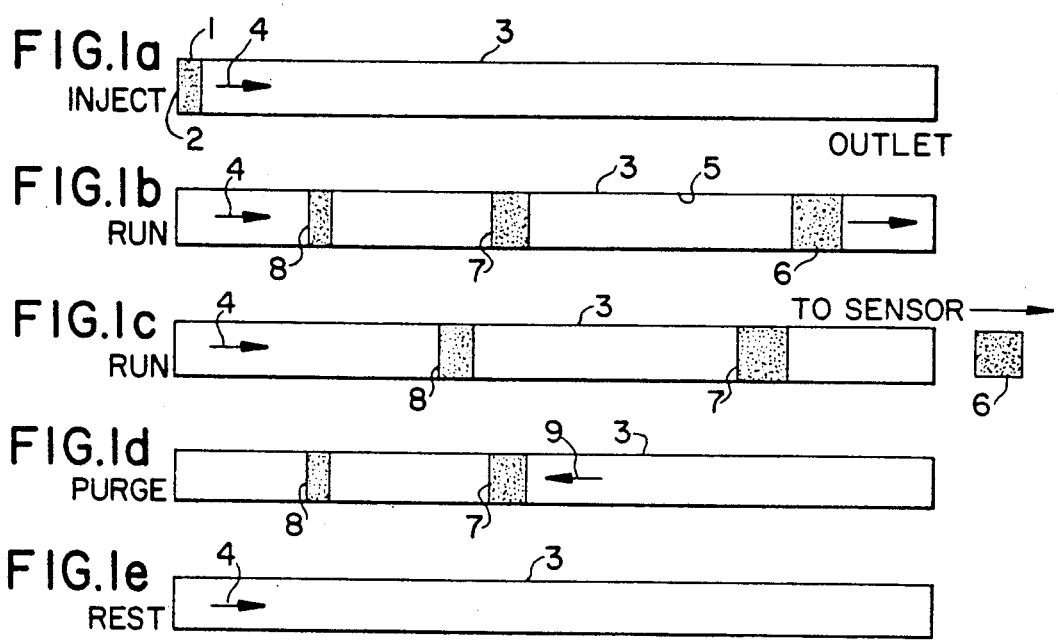
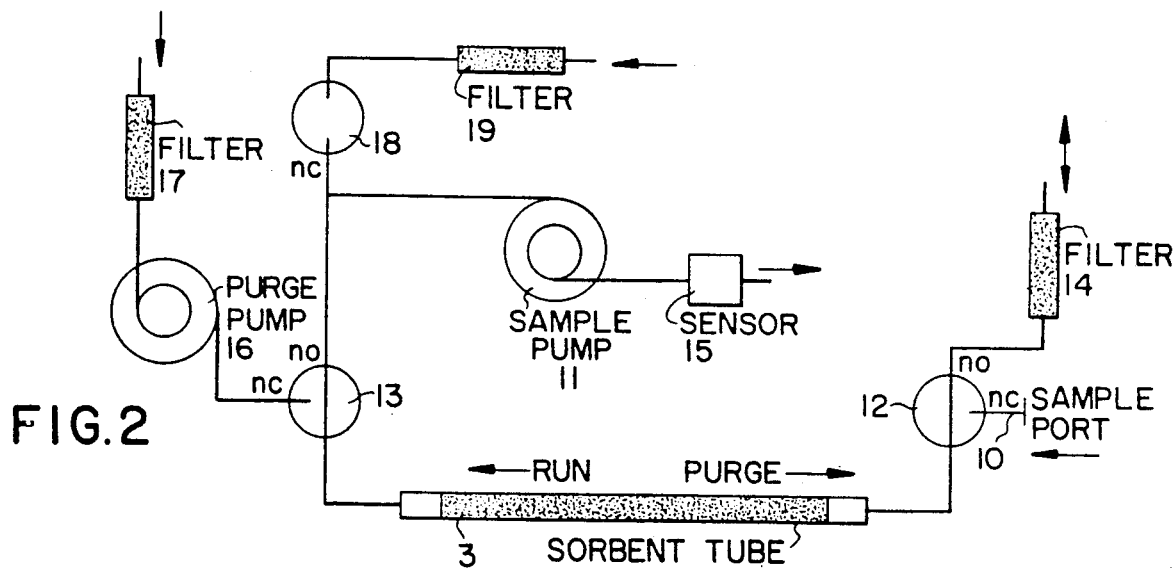
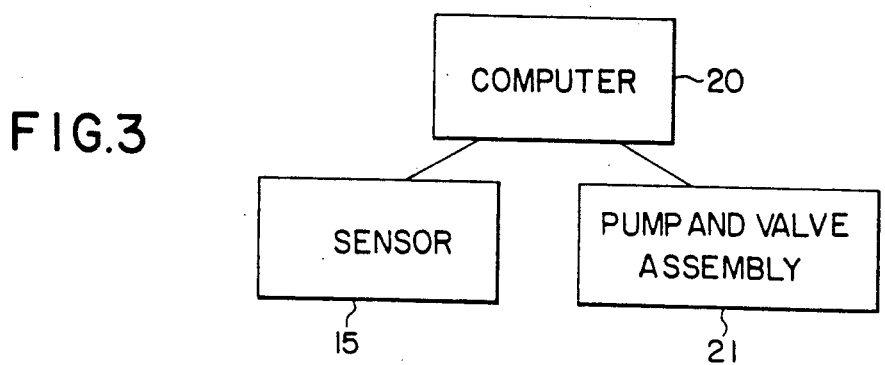

SORPTION SEPARATION APPARATUS AND METHODS

BACKGROUND OF THE INVENTION

This invention relates to apparatus and methods for separating volatile analytes from gaseous mixtures, especially from mixtures containing potentially interfering compounds, and measuring the concentrations of the analytes.

Gas chromatography is widely used to fractionate gaseous mixtures into a stream of purer components eluting at different time intervals, with the most volatile components or those having the lowest molecular weights usually eluting first and the least volatile components (with heaviest molecular weights) eluting after much longer times. Such fractionation may be practical when the elution times are not excessive, e.g., of the order of 10 minutes or less. However, when interferences (i.e., interfering compounds) may be present that take longer times to elute, then erroneous analytical results may be obtained if the duration of an analytical cycle is shorter than the elution time of the least volatile (or "heaviest") interference.

It is a purpose of our invention to provide means for separating volatile components from a gaseous mixture within relatively brief spans of time.

It is another object of our invention to permit accurate measurements of the concentrations of these volatile components without introduction of errors due to less volatile ("heavier") interferences.

It is a further object of this invention to provide cost-effective means for selectively monitoring the concentration of volatile analytes in gaseous mixtures.

It is a particular object of our invention to provide improved means for monitoring carbon monoxide, methanol, methylene chloride, and formaldehyde in the presence of potential interferences.

It is still a further object of our invention to improve the reliability of gas chromatographic analyses involving volatile analytes, especially with the use of portable gas chromatographs.

It is yet another object of our invention to improve the speed and selectivity of chromatographic analyses.

Yet another object of our invention is to provide a convenient and simple separation method that can be implemented for a variety of analytes and with various detection means.

SUMMARY OF THE INVENTION

Briefly, our invention consists of passing gaseous samples through a tube containing a sorbent material, the sorbent having stronger affinity towards the interferences than toward the analyte, so that the analyte elutes from the tube before the interferences. The eluting analyte is passed through a chemical sensor, which measures its concentration. When all or most of the analyte has eluted from the tube, clean air or another carrier gas is passed through the tube in reverse direction, so as to rapidly remove the interferences from the sorbent in preparation for the next analytical cycle. To speed up the last step, the reverse flow may be much faster than the forward flow. Therefore, the minimum cycle time is determined mainly by the duration of the forward flow, i.e., the time required to elute the analyte from the tube, which is relatively short for volatile analytes. The complete cycle and a succession of such cycles are preferably automated.

A variation of this process is where the interference elutes before the analyte, is discarded, and the analyte only is allowed to pass to the detector.

BRIEF DESCRIPTION OF THE DRAWINGS

Our invention is best explained with reference to the drawings, in which:

FIGS. 1a–1e is a schematic diagram showing the spatial distributions of the components of a gaseous sample at various stages of an analytical cycle;

FIG. 2 is a block diagram showing the components required to effectuate the cycle of FIG. 1 in a preferred embodiment of the invention;

FIG. 3 is a schematic block diagram showing the interactions of some components of FIG. 2 with a programmed computer or microprocessor-controller;

DESCRIPTION OF THE PREFERRED EMBODIMENTS

Figure 4:
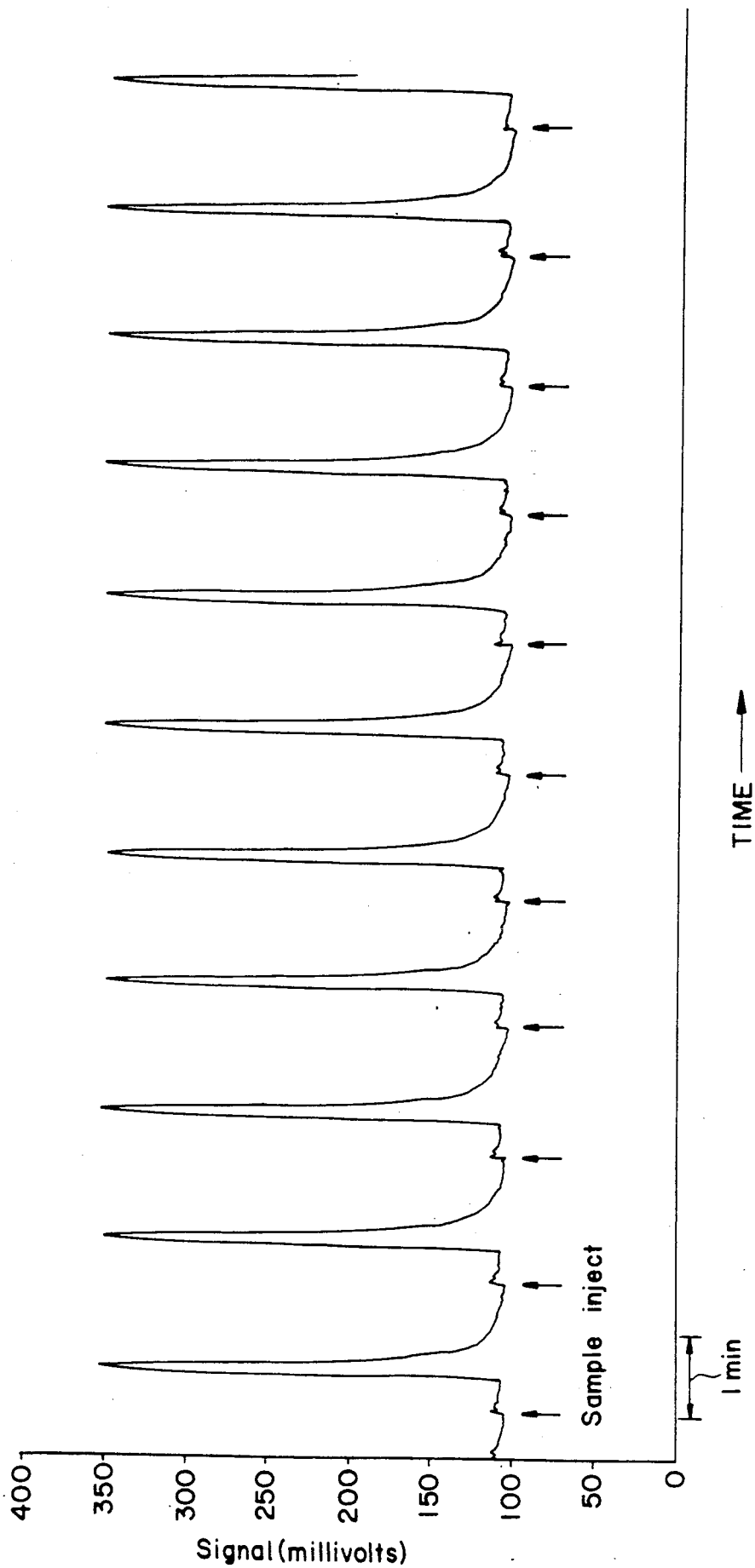
FIG. 4 is a typical recording of sensor signals obtained in experiments with the embodiment of FIG. 2.

Gas chromatography is one of the most widely used analytical techniques for separating volatile compounds. In its simple form, it is a long tube containing a stationary phase, usually nonvolatile oil or grease. A pure gas, called the mobile phase or carrier gas, passes through the tube at a constant rate. If a small volume of a gaseous sample is injected into the carrier gas at the inlet of the tube, it will be subject to two opposing forces: (a) the forward movement of the carrier gas tending to sweep the sample through the column, and (b) the tendency to partition, i.e., adsorb onto or dissolve into the stationary phase. The actual rate of movement of the injected gas through the column is a compromise between the two forces. Different compromises are reached for different compounds, and so a sample consisting of a mixture tends to separate into the individual components, each moving at an independent rate. Finally, each compound exits from the column at a distinct time called "retention time". Suitable detection devices can measure the concentrations of effluent gases as a function of time.

Gas chromatography is an extremely versatile technique, and has been applied to a number of environmental problems. Automation of the method, and adaptation to portable instruments, has been repeatedly attempted. Even though many portable gas chromatographs are available on the market today, they have a serious reputation for unreliability. The method disclosed herein will avoid some of the most severe problems, and make gas chromatography more useful for certain kinds of analysis.

FIGS. 1a–1e illustrate the principle of the method, which we call Frontal Analysis by Periodic Reversal of Flow (FAPROF). The method is most useful when a combination of carrier gas and stationary phase can be found such as to cause the analyte of interest to elute from the column before any other component. The steps in a FAPROF analysis are as follows:

In Step 1, depicted in FIG. 1a, a gaseous sample 1 is injected at the inlet 2 of a gas chromatographic column or tube 3 into a forward-moving stream of carrier gas indicated by the arrow 4.

In Step 2a, depicted in FIG. 1b, the forward movement of the carrier gas and partitioning by a sorbent 5 (which covers the inner wall of column 3) cause the components of sample 1 to separate into discreet plugs 6,7,8,... of which the leading plug 6 contains the volatile analyte of interest.

In Step 2b, shown in FIG. 1c, the analyte-containing plug 6, which is closest to the sensor and forwardmost in the analytical system at this time, is eluted from column 3, while the lagging plugs 7,8,... remain in the column.

In Step 3, depicted schematically in FIG. 1d, the flow of carrier gas is reversed, as indicated by arrow 9, and the remaining plugs, 7,8,... are flushed back from column 3 through inlet 2.

In Step 4, depicted in FIG. 1e, the purge of the heavier interferences having been completed, the flow of the carrier gas is returned to the forward direction, and the column is ready for the start of a new cycle.

The reversal of carrier gas flow in Step 3 assures that all substances that enter column 3 are fully purged. In ordinary gas chromatography, the slowest, moving components limit the time between successive analyses. In the FAPROF method, the slowest components have a shorter distance to move in order to leave the column; in principle, all the interferences should exit the column at the same time, regardless of their rate of movement. Furthermore, since the rate of carrier flow in the purge step can be raised as high as necessary, the duration of Step 3 can be made brief in comparison with that of Steps 2a and 2b.

One preferred embodiment of our invention is shown in the block diagram of FIG. 2. Sampled air from a sample port 10 together with carrier gas are drawn by a sample pump 11 through a solenoid valve 12, sorbent tube 3, and a second solenoid valve 13. The carrier gas may consist of ambient air from which any analyte and interferences have been removed by a chemical filter 14. The carrier stream drawn by pump 11 is fed to chemical sensor 15, which measures the concentration of analyte eluting from tube 3.

To reverse the carrier flow, a purge pump 16 draws analyte, and interference-free air from a chemical filter 17 and forces it through valve 13, sorbent tube 3, valve 12, and filter 14, in purified form, out into the ambient air. At the same time, a third solenoid valve 18 connects sample pump 11 to a third chemical filter 19 to effect purging of sensor 15 with analyte-free and interference-free air.

The apparatus of FIG. 2 has been used to determine the concentration of hydrogen sulfide in the presence of several interfering organosulfur compounds. All connecting tubing in FIG. 2 was made of polyethylene. The sorbent tube was a Supelco 6 mm i.d. × 13 cm long gas chromatography column packed with Carbopak B/1.5% XE.60/1.0% $H_3PO_4$. This sorbent was selected from Supelco literature indicating that hydrogen sulfide has a very short retention time on this sorbent relative to other sulfur gases. The effluent from the column entered an amperometric hydrogen sulfide sensor (made by Transducer Research, Inc.) which is sensitive to most sulfur gases. The solenoids shown in the diagram were controlled by an Onset Computer Corp. Tattletale IV datalogger/computer.

The four phases of operation are shown in Table 1. In the REST phase, all solenoids are not energized, and the carrier gas (clean air) is flowing in the forward direction through the column. In the INJECT phase, solenoid 12 is energized for a specific period of time, so as to admit a precise volume of sample to the air stream. The next phase, RUN, is like the REST phase, except that the duration of the phase is limited, and the supervising computer is watching the output. When the hydrogen sulfide peak has passed, the PURGE phase begins. The carrier stream, possibly at a different pressure, is passed through the sorbent tubes in the reverse direction. Another stream of air, through solenoid 18, purges the sensor. After a sufficient time, the instrument returns to the REST phase.

TABLE 1

| Phases of operation of the FAPROF device of FIG. 2. | | | |
|---|---|---|---|
| Phase | Solenoid 12 | Solenoid 13 | Solenoid 18 |
| REST | off | off | off |
| INJECT | on | off | off |
| RUN | off | off | off |
| PURGE | off | on | on |

The components of FIG. 2 interact with a computer or microprocessor-controller 20 as indicated by the block diagram of FIG. 3. The computer or microprocessor 20 actuates and monitors the operation of the pumps 11 and 16 and of the valves 12, 13, and 18, all of which are represented in FIG. 3 by a single "pump and valve assembly" block 21. When each of the pumps and valves are performing as specified in Table 1, the absence of signal from sensor 15 indicates an absence or very low concentration of the analyte in the gas mixture. Controller 20 can then increase the duration of the INJECT phase so as to increase the sensor signal for low analyte concentrations (vide infra).

Experiments were done with the apparatus of FIG. 2, using hydrogen sulfide concentrations in the 20-35 ppm range, ethyl mercaptan in the 11-20 ppm range, and mixtures of the two. The RUN time was adjusted to 50 seconds to allow the $H_2S$, peak to reach a maximum. It was not necessary for the peak to be completely eluted for a quantitative analysis; only a peak maximum was necessary. A typical recording of the sensor signals is shown in FIG. 4. Only the $H_2S$ peaks show up in the recording. The mercaptan is not seen because the purge phase begins before it can exit from the column. In these experiments, the INJECT phase was adjusted to 15 seconds, the RUN phase to 70 seconds, and the PURGE phase to 90 seconds.

In the recording of FIG. 4, the sensor signal is shown in millivolts. To convert it to units of the concentration of $H_2S$ in the sampled gas, it is necessary to calibrate the sensor using a standard gas of known analyte concentration and a fixed duration of the INJECT phase. For the same fixed duration, the height of the recorded peaks will be approximately proportional to the analyte concentration in the sampled air. If the analyte concentration becomes so small that the recorded peaks are not accurately measurable, the sensitivity can be improved by increasing the duration of the INJECT phase so as to introduce a greater amount of analyte into the sorbent tube, thereby increasing the peak height. On the other hand, if the analyte concentration is so high as to yield peaks that are off-scale, the INJECT phase can be shortened so as to introduce a smaller amount of analyte into the column, thereby reducing the peak height. In either case, the actual analyte concentration in the sampled air will be proportional to the measured peak height divided by the duration of the INJECT phase. Since that duration can be automatically adjusted upward or downward by the computer or microprocessor-controller 20' depending on the last sensor read-out of the peak height, the system of FIG. 2 can be seen to provide an autoranging feature for varying analyte concentrations.

Of course, our invention can be applied to measurements of the concentrations of a number of other volatiles that currently defy attempts to being monitored in a cost-effective and selective manner. These include methanol, acetaldehyde, methylene chloride and formaldehyde. For each of these, there exists a sorbent from which the compound elutes before other potential contaminants.

Figure 5:
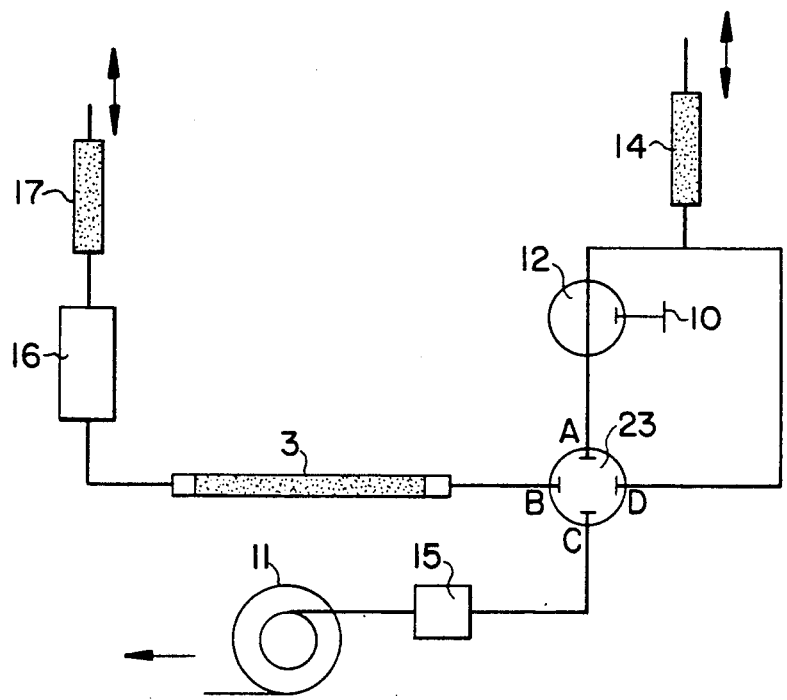
FIG. 5 is a block diagram applicable to an alternative embodiment of our invention.

In a variation of the preceding embodiment, the gaseous sample 1 of FIG. 1 may consist of a mixture of hydrogen ($H_2$) and carbon monoxide (CO). With some sensors, such as infrared or thermal conductivity detectors, it is easy to distinguish between $H_2$, and CO, but such sensors may be subject to other interferences, such as hydrocarbons. Electrochemical, especially amperometric, sensors can distinguish between CO and hydrocarbons, but not between CO and $H_2$. If sensor 15 is an amperometric detector, it is possible to measure the concentration of CO in a gaseous mixture by rearranging most of the components of FIG. 2 as shown in FIG. 5 and by substituting a four-port valve 23 for valves 13 and 18. The arrangement of FIG. 5 applies to those cases where the interference consists of the compound having the shortest retention time, as represented by the forwardmost plug 6 of FIG. 1. For $H_2$/CO mixtures, plug 6 will comprise the $H_2$ interference which is purged in the following sequence. As in FIG. 2, the gaseous sample is first introduced through sample port 10 and valve 12 and drawn into the inlet of column 3 (which may comprise 3 grams of molecular sieve in a 15 cm column) via valve 23, with ports A and B interconnected. Thereafter, valve 12 is switched to pass carrier gas (purified air) in the forward direction through filter 14, valves 12 and 23 (with ports A and B interconnected), column 3, purge pump 16 and filter 17 long enough (e.g., about 5-10 seconds) to remove the $H_2$ interference in filter 17. Thereafter, pump 16 is immediately reversed or allowed to idle as valve 23 is switched to interconnect ports B and C so as to allow carrier gas entering through filter 17 and any analyte remaining in column 3 to be drawn backwards by pump 11 into valve 23 and thence fed to sensor 15. Finally, sensor 15 may be purged by interconnecting ports C and D so as to pump carrier gas from filter 14 through sensor 15.

Figure 6:
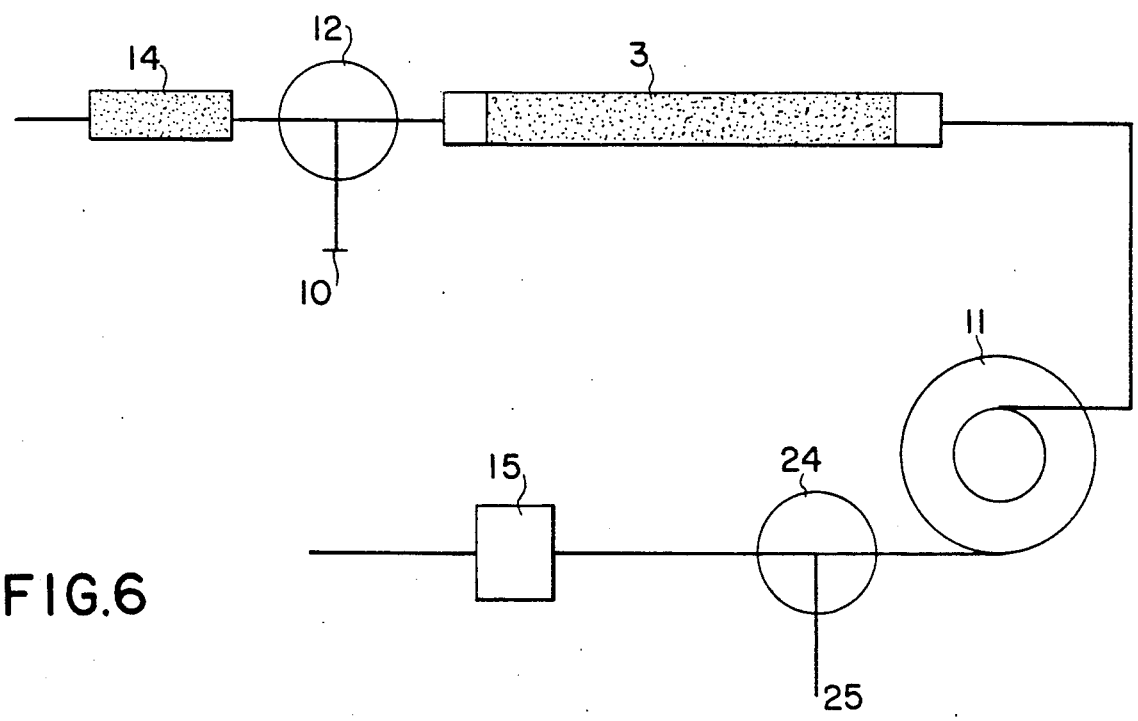
FIG. 6 is a block diagram of an alternative flow arrangement applicable to the separation of two volatile components.

A simpler alternative to the arrangement of FIG. 5 is shown in FIG. 6. Here again, the $H_2$/CO mixture is injected through sample port 10 and valve 12 into the inlet of column 3, which may comprise 3 g of molecular sieve in a 15 cm column. With carrier gas pumped at a rate of 50 mL/min, at a temperature of about 20° C., the $H_2$ elutes in 5-10 sec, and is pumped out through valve 24 and vent 25 which may include a hydrogen-burning catalyst or filter (not shown). Then valve 24 is switched so as to feed the remaining eluent from column 3 into sensor 15. With this simpler arrangement, a reverse purge is usually unnecessary.

The problem of detecting CO in the presence of $H_2$ is important in catalyst research, in catalytic processes, and in semiconductor manufacture. The scheme of either FIG. 5 or FIG. 6 makes it possible to monitor CO in $H_2$/CO mixtures with amperometric sensors, which offer several advantages over alternative detectors (such as small size, portability, and ability to discriminate between CO and hydrocarbons).

There will now be obvious to those skilled in the art many modifications and variations of the afore-disclosed embodiments, which, however, will remain within the scope of our invention if defined by the following claims.

We claim:

1. A method of selectively detecting an analyte in a gaseous mixture by a chemical sensor comprising the steps of
   (a) pumping ambient air through a chemical filter so as to purify the air from those constituents to which said sensor is responsive,
   (b) pumping the purified air through a sorbent-containing tube and through said sensor,
   (c) drawing a portion of said gaseous mixture into a sample port,
   (d) flushing said portion with purified air from the sample port into said sorbent tube, through an inlet end of the tube,
   (e) directing analyte-containing eluent from the sorbent tube into said sensor, and
   (f) preventing at least one other mixture component to which said sensor is responsive from reaching the sensor, said sorbent having a different retentivity for the analyte than for another component of the gaseous mixture to which the sensor is responsive.

2. The method of claim 1, wherein said steps are effected by a pump-and-valve means controlled by a control means, said control means causing valves appertaining to the pump-and-valve means to be sequentially switched so as to direct the pumped fluids in concordance with said steps.

3. The method of claim 2, comprising the further step of purging the sensor, the sorbent tube, and the pump-and-valve means from said other component.

4. The method of claim 3, wherein said purging step includes venting said other component.

5. The method of claim 3, wherein said purging step comprises the step of reversing the flow of air through said tube following elution of analyte into the sensor, so as to cause said other component of the mixture to elute through the inlet end of the tube.

6. The method of claim 5, wherein the flow-reversing step effects a rate of reverse flow that is faster than that of the flow in the forward direction.

7. The method of claim 3, comprising the further steps of disposing said sensor to yield a signal that is a function of the concentration of the analyte that is reaching the sensor and deducing from said signal the concentration of the analyte in the mixture.

8. The method of claim 7, comprising the further step of adjusting the volume of said portion so as to improve the accuracy of the sensor signal.

9. The method of claim 7, wherein said sensor is an amperometric sensor.

10. The method of claim 9, wherein said analyte is carbon monoxide and said other mixture component is hydrogen.

11. The method of claim 9, wherein said analyte is hydrogen sulfide and said other mixture component is an organosulfur compound.

12. The method of claim 11, wherein said organosulfur compound is a mercaptan.

13. The method of claim 7, wherein said analyte appertains to the family of compounds including carbon monoxide, hydrogen sulfide, methanol, methylene chloride, and formaldehyde and said other mixture component is a compound of heavier molecular weight.

14. The method of claim 7, which includes controlling the pump-and-valve means by, and feeding the sensor signals to, programmed electronic circuitry.

15. Portable apparatus for detecting an analyte in a gaseous mixture comprising:
(a) a selective chemical sensor which generates signals responsive to the analyte in an air stream,
(b) a sorbent-containing tube,
(c) a pump-and-valve means interconnected with said tube and said sensor and controlling the analyte flow through said tube and through said sensor,
(d) a chemical filter means for removing from ambient air those air constituents to which said sensor is responsive,
(e) a control means for controlling the operation of said pump-and-valve means, and
(f) a signal-processing means for interpreting the signals from said sensor,
said sorbent tube having a different retentivity for the analyte than for at least one other component of the gaseous mixture to which said sensor is responsive, and said control means being programmed to cause the pump-and-valve means to pass purified ambient air through said tube and said sensor, draw a portion of the gaseous mixture into a sample port, flush the mixture with purified air from the sample port into said sorbent tube, direct analyte-containing eluent from the sorbent tube into said sensor, and prevent at least one other mixture component to which said sensor is responsive from reaching said sensor.

16. Apparatus of claim 15, wherein said pump-and-valve means includes means for purging the apparatus from said other mixture component, said purging means being interconnected with said sorbent tube.

17. Apparatus of claim 16, where said purging means includes a vent.

18. The apparatus of claim 17, wherein said filter means comprises two chemical filters, and said pump-and-valve means comprises two interconnected electrically controllable valves, one of said valves being connected through different ports to said sensor and to said tube, one air pump, connected to said sensor, for flowing either purified or analyte-containing air through the sensor, and a second air pump, connected to said tube, for drawing the portion of the gaseous mixture into a sample port and purging the apparatus of an interfering compound that is lighter than the analyte.

19. The apparatus of claim 17, wherein said pump-and-valve means comprises two electrically controllable valves and one air pump for drawing purified air or said portion into the sorbent tube and for pushing analyte-containing air through the sensor and said other mixture component through a vent, the first of said valves being interposed in a flow line between said sensor and said pump, with the pump being interposed in a flow line between said first valve and said tube, and the tube being interposed in a flow line between the pump and the second of said valves.

20. The apparatus of claim 19, wherein said vent comprises a chemical filter or a hydrogen-burning catalyst.

21. Apparatus of claim 16, wherein said sensor is an amperometric sensor.

22. Apparatus of claim 16, wherein said purging means comprises means for reversing the flow of air through said tube following elution of analyte into the sensor, so as to cause said other component of the mixture to elute through the inlet end of the tube.

23. The apparatus of claim 22, wherein said flow-reversing means is capable of effecting a rate of reverse flow that is faster than that of the flow in the forward direction.

24. The apparatus of claim 22, wherein said filter means comprises three chemical filters, and said pump-and-valve means comprises three electrically controllable valves, one air pump, connected to a first and second of said valves, for drawing the portion of the gaseous mixture into a sample port and flowing either purified or analyte-containing air through the sensor, and a second air pump, connected to said second valve, for flowing purified air through the sorbent tube in reverse direction.

25. The apparatus of claim 16, wherein said sensor is disposed to yield a signal that is a function of the concentration of the analyte that is passing through the sensor and wherein said signal-processing means includes means for deducing from said signal the concentration of the analyte in the mixture.

26. The apparatus of claim 25, wherein said signal-processing and control means include a computer or microprocessor-controller.

27. The apparatus of claim 26, including means for automatically adjusting the volume of said portion of the gaseous mixture so as to improve the accuracy of the sensor signal.

* * * * *